United States Patent
Chen

(10) Patent No.: US 9,220,921 B2
(45) Date of Patent: Dec. 29, 2015

(54) METHOD AND SYSTEM FOR RADIOISOTOPE ION BEAM GAMMA THERAPY

(75) Inventor: Sung-Wei Chen, Singapore (SG)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 280 days.

(21) Appl. No.: 13/063,428

(22) PCT Filed: Sep. 1, 2010

(86) PCT No.: PCT/SG2010/000318
§ 371 (c)(1),
(2), (4) Date: Mar. 10, 2011

(87) PCT Pub. No.: WO2012/030297
PCT Pub. Date: Mar. 8, 2012

(65) Prior Publication Data
US 2012/0053389 A1   Mar. 1, 2012

(51) Int. Cl.
*A61N 5/10* (2006.01)

(52) U.S. Cl.
CPC .............. *A61N 5/1042* (2013.01); *A61N 5/1071* (2013.01); *A61N 2005/1052* (2013.01); *A61N 2005/1072* (2013.01)

(58) Field of Classification Search
CPC .............. A61N 5/1042; A61N 5/1071; A61N 2005/1072; A61N 2005/1052
USPC .................................... 600/1; 250/369, 492.3
See application file for complete search history.

(56) References Cited

U.S. PATENT DOCUMENTS

| | | | | |
|---|---|---|---|---|
| 6,137,110 | A * | 10/2000 | Pellin et al. | 250/423 P |
| 6,683,318 | B1 * | 1/2004 | Haberer et al. | 250/492.3 |
| 7,176,470 | B1 * | 2/2007 | Evans et al. | 250/492.21 |
| 7,586,110 | B1 * | 9/2009 | Low | 250/492.21 |

(Continued)

FOREIGN PATENT DOCUMENTS

| | | |
|---|---|---|
| EP | 1642617 B1 | 5/2008 |
| JP | 2008173299 A * | 7/2008 |

OTHER PUBLICATIONS

Urakabe et al. "Spot Scanning Using Radioactive 11C Beams for Heavy-Ion Radiotherapy." Jpn. J. Appl. Phys. vol. 40 (2001) 99. 2540-2548.*

(Continued)

*Primary Examiner* — Navin Natnithithadha
*Assistant Examiner* — Kaylee Wilson
(74) *Attorney, Agent, or Firm* — Foley & Lardner LLP

(57) ABSTRACT

A method includes directing an ion beam at a tissue. Ions of the ion beam can include positron emitters, such as carbon-11, nitrogen-13, oxygen-15, and fluorine-17. The ions can ionize at least a portion of the tissue and the positron emitters can irradiate the at least a portion of the tissue. The ion beam may be generated with a cyclotron, a synchrotron, or a particle accelerator. The ion beam may be targeted at the tissue using a stereotactic targeting system, clinical dosimetry system, or a positron emission tomography system such that a delivered energy of the ions peaks throughout a volume of the targeted portion of the tissue. The ions may damage a cell in the tissue, and positrons produced, in vivo, by the positron emitters may combine with electrons to create gamma rays that damage the cell in the course of a combination ion beam therapy and brachytherapy treatment.

20 Claims, 4 Drawing Sheets

(56) References Cited

U.S. PATENT DOCUMENTS

| | | | |
|---|---|---|---|
| 2006/0018827 A1 | 1/2006 | Dadachova et al. | |
| 2008/0135764 A1 | 6/2008 | Braess | |
| 2008/0272284 A1* | 11/2008 | Rietzel | 250/252.1 |
| 2009/0256078 A1 | 10/2009 | Mazin | |
| 2009/0309038 A1* | 12/2009 | Balakin | 250/396 R |

OTHER PUBLICATIONS

Nishio et al., JP 2008173299 A English Translation, Jul. 2008.*
Kanazawa et al., Application of an RI-Beam for cancer therapy: In vivo verification of the ion-beam range by means of positron imaging:, *Nucl Phys A*, 2002, 701(1-4):244-252.
International Search Report and Written Opinion for PCT/SG2010/000318, mailed Oct. 20, 2010 (12 pages).
Welsh, James S., "Beta Decay in Science and Medicine," *American Journal of Clinical Oncology*, 2007, 30(4):437-439.
"Pulsar® PET Isotope Production System," AccSys Technology, Inc. Accessed at http://www.accsys.com/pulsar.html, Accessed on May 16, 2012, pp. 4.
Castro, J.R. et al., "Experience in Charged Particle Irradiation of Tumors of the Skull Base 1977-1992," International Journal of Radiation Oncology Biology Physics, vol. 29, Issue 4, pp. 647-655, Jul. 1, 1994.
Castro, J.R., "Clinical Programs: A Review of Past and Existing Hadron Protocols," in Amaldi, U. et al. (eds.) Advances in Hadron Therapy, Elsevier: Amsterdam, Netherlands. pp. 79-94 (1997).
Gueulette, J., et al., "Proton Relative Biological Effectiveness (RBE) for Survival in Mice After Thoracic Irradiation with Fractionated Doses," International Journal of Radiation Oncology Biology Physics, vol. 47, Issue 4, pp. 1051-1058, Jul. 1, 2000.
Hartmann, G.H., et al., "Determination of Water Absorbed Dose in a Carbon Ion Beam Using Thimble Ionization Chambers," Physics in Medicine and Biology, vol. 44, pp. 1193-1206, 1999.
International Atomic Energy Agency (Ed.), "Absorbed Dose Determination in External Beam Radiotherapy," Technical Report Series No. 398 (TRS-398), 2000.
Jakel, O., "State of the Art in Hadron Therapy," AIP Conference Proceedings, vol. 958, pp. 70-77, Jul. 8-19, 2007.
Kanai, T., et al., "Biophysical Characteristics of HIMAC Clinical Irradiation System for Heavy-Ion Radiation Therapy," International Journal of Radiation Oncology Biology Physics, vol. 44, Issue 01, pp. 201-210, Apr. 1, 1999.
Kanai, T., et al., "Examination of GyE System for HIMAC Carbon Therapy," International Journal of Radiation Oncology Biology Physics, vol. 64, Issue 2, pp. 650-656, Feb. 1, 2006.
Kubota, N., et al., "A Comparison of Biological Effects of Modulated Carbon-Ions and Fast Neutrons in Human Osteosarcoma Cells," International Journal of Radiation Oncology Biology Physics, vol. 33, No. 1, pp. 135-141, Aug. 30, 1995.
Sisterson, J. (ed.), "Particle Newsletter," No. 36, pp. 1-11, Jul. 2005.
Uzawa, A., et al., "Comparison of Biological Effectiveness of Carbon-Ion Beams in Japan and Germany," International Journal of Radiation Oncology Biology Physics, vol. 73, Issue 5, pp. 1545-1551, Apr. 1, 2009.
Wilson, R.R., "Radiological Use of Fast Protons," Radiology, vol. 47, No. 5, pp. 487-491, Nov. 1946.

* cited by examiner

METHOD AND SYSTEM FOR RADIOISOTOPE ION BEAM GAMMA THERAPY

This is a National Stage application of PCT/SG2010/000318, filed Sep. 1, 2010, the entirety of which is hereby incorporated by reference in its entirety.

BACKGROUND

The following description is provided to assist the understanding of the reader. None of the information provided or references cited is admitted to be prior art.

Tuned-frequency energy sources can be used to selectively deliver energy to a tumor for improved therapeutic outcomes or to address difficult-to-treat diseases. For example, some tuned-frequency energy sources include focused ultrasound, gamma ray knives, and proton beams. Each energy source has advantages and disadvantages.

Proton therapy utilizes externally generated beams of protons to destroy cancer cells through an ionizing, DNA-damaging mechanism. Proton therapy can be applied clinically to a range of cancers, such as in the uveal tract, cervical spine, pituitary gland, skull, brain stem, and spinal cord. Proton therapy has a well-defined range, or penetration depth, in tissue. Much of the energy transfer from the protons takes place at the end of the linear trajectory of the protons, represented by a Bragg peak. By modulating the energy of incoming protons, the biologically effective dose may be conformed to different depths, spatially localizing the dose to the tumor. This total conformed radiation dose can be represented by the Spread-Out Bragg Peak (SOBP).

Gamma therapy such as a gamma knife therapy or brachytherapy utilizes gamma rays to destroy cancer cells. Gamma knife therapy includes directing external gamma rays at a tumor. The gamma rays can be generated by a radioactive cobalt source. Brachytherapy includes implanting radioactive seeds next to a tumor. The radioactive material in the seeds emits gamma rays as the material decays. The gamma radiation causes cell death by damaging cell DNA. Gamma radiation varies in efficacy and mode because of different energetic qualities, biological absorption, and other factors.

Improved radioisotope energy sources can offer new treatment modalities that are likely to improve cost effectiveness, economics, therapeutic outcome, and may enable treatment of currently intractable disease.

SUMMARY

The present technology provides a method, system and apparatus useful for radioisotope ion beam gamma therapy.

In one aspect, the present technology provides a treatment method including directing an ion beam at a tissue. The ion beam can include ions such as positron emitters. The ions and positron emitters can ionize at least a portion of the tissue and the positron emitters can irradiate the at least a portion of the tissue.

In another aspect, the present technology provides an apparatus including an ion beam apparatus configured to generate and to direct an ion beam at a tissue. The ion beam can include ions such as positron emitters. The ions and positron emitters can ionize at least a portion of the tissue and the positron emitters can irradiate the at least a portion of the tissue.

In another aspect, the present technology provides an article of manufacture including a computer-readable medium having computer readable instructions stored is thereon that, if executed by a computing device, cause the computing device to perform operations including directing an ion beam at a tissue. The ion beam can include ions such as positron emitters. The ions and positron emitters can ionize at least a portion of the tissue and the positron emitters can irradiate the at least a portion of the tissue.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
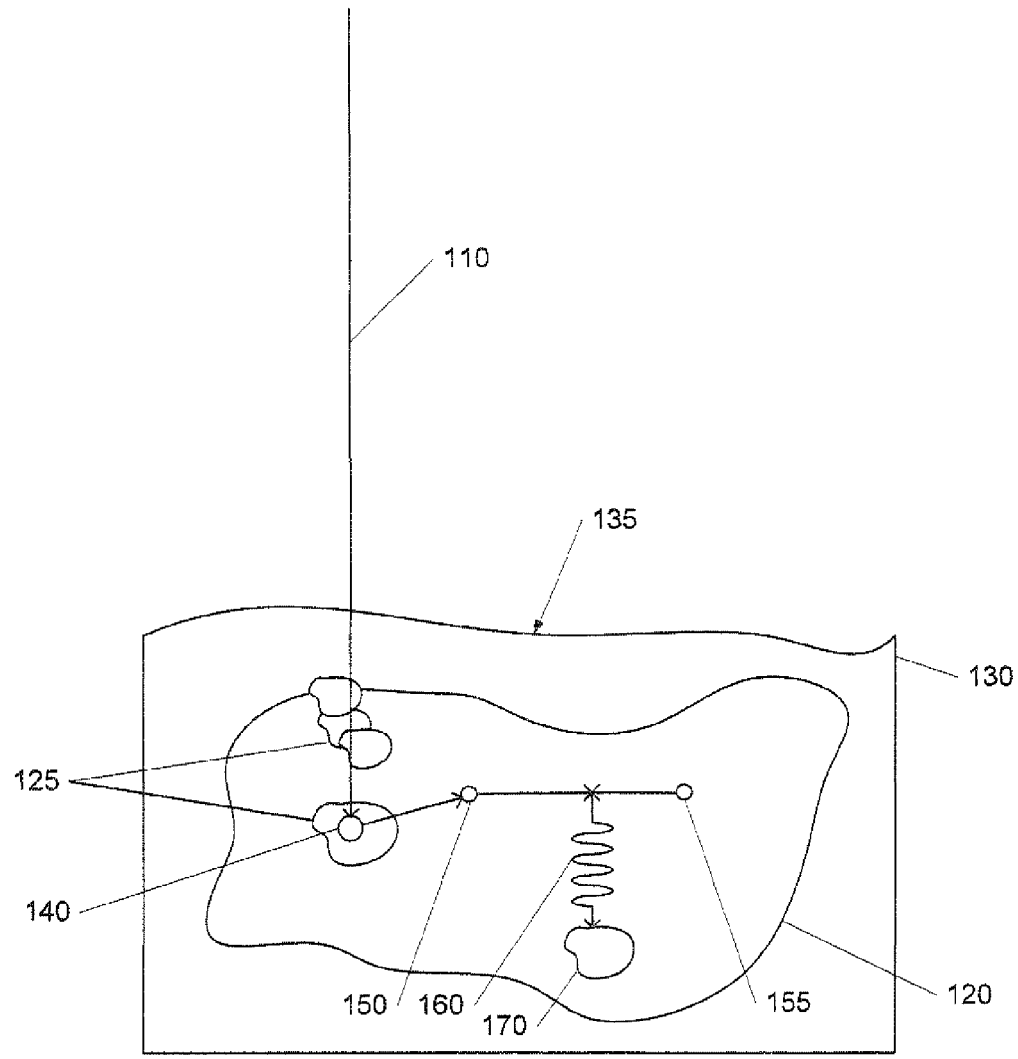
FIG. 1 is a diagram of radioisotope ion beam gamma therapy in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Described herein are illustrative systems, methods, computer-readable media, etc. for radioisotope ion beam gamma therapy. Ion beams of radioisotopes can be directed to a target for ion beam therapy and in vivo gamma ray therapy (brachytherapy). For example, ions of short-lived, positron-emitting isotopes can be focused on a tissue. The ionizing energy of the ions can transferred in a narrow spatial range described by the Bragg peak of the ionic species. The ionizing energy of the ions can damage the tissue thereby causing cell death. Positrons emitted by the isotopes can annihilate with electrons to emit 511 keV gamma rays. The gamma rays can irradiate the tissue thereby causing damage and subsequent cell death. The emitted gamma rays can also be used to image the treatment area by, for example, positron emission tomography (PET) for dosimetry and localization. Advantageously, the radioisotope ion beam gamma therapy can employ recent, more efficient particle accelerator technologies making radioisotope ion beam gamma therapy more cost effective.

Referring to FIG. 1, a diagram of radioisotope ion beam gamma therapy in accordance with an illustrative embodiment is shown. In radioisotope ion beam gamma therapy, an ion beam 110 is directed at a target area 120 of a tissue 130. The ion beam 110 can include short-lived, positron-emitting radioisotopes, including, but not limited to, $^{11}$C (Carbon-11), $^{13}$N (Nitrogen-13), $^{15}$O (Oxygen-15), and $^{18}$F (Fluorine-18). The ion beam 110 can include one type of ion or many types of ions. The positron emitters can include at least one isotope of an element of the ions. In one illustrative embodiment, the positron-emitting ions can have an atomic number less than, but not limited to, eleven (i.e., an element with a proton count less than that or equal to neon). Alternatively, more than one ion beam can be directed at the target area 120 of the tissue 130. For example, a first ion beam can include a first-type of ion (e.g., Carbon-11) and a second ion beam can include a second-type of ion (e.g., Oxygen-15).

Proton therapy is characterized by low linear energy transfer (LET), but heavier particles, such as the positron emitters listed above, possess a high LET. The heavier ions exhibit a very sharp Bragg peak (explained further below) compared to protons. The sharp Bragg peak can be used to deliver high, well-defined energy spectra to tumors while minimizing neighboring tissue damage.

The tissue 130 can be any tissue such as human and non-human tissues. The tissue 130 can be part of, but not limited to, for example, the uveal tract, cervical spine, pituitary gland, skull, brain stem, and spinal cord. The target area 120 of the tissue 130 can be cancerous cells such as a tumor or any other cells or biological material.

The ions of ion beam 110 strike a surface 135 of the tissue 130 and begin to penetrate into the tissue 130. As the ions pass through cells 125, some of the cells 125 can be damaged by the ions and/or ionization. For example, the DNA and/or RNA of cells 125 can be damaged, the cell walls of cells 125 can be damaged, the mitochondria of cells 125 can be damaged, etc. Some of cells 125 can experience cell death as a result of the damage. When the ions move through the tissue 130, the ions ionize atoms of the tissue 130 and deposit a dose along the path. A dosage peak occurs as the ions come to rest because the interaction cross section increases as the ions' energy decreases.

The ions of ion beam 110 are energized such that the ions release the majority of their energy at about a targeted depth range. In one illustrative embodiment, the targeted depth range can be described as a Bragg peak. The Bragg peak for a particle can be measured as a function of energy and/or ions in a standard medium, for example, but not limited to water. Illustrative methods of measuring and calculating the effective dose and energy of ions in biological applications are discussed in Jakel, O., "State of the Art in Hadron Therapy," in CP958, Nuclear Physics Methods and Accelerators in Biology and Medicine, eds. C. Granja, et al. (2007) 70-77; and Hartmann, G. H., et al., "Determination of Water Absorbed Dose in a Carbon Ion Beam Using Thimble Ionization Chambers," Physics in Medicine and Biology (1999) 44: 1193-1206, which are both incorporated herein by reference in their entirety.

In a typical application, the target depth range is about 0-180 mm below the surface 135 of the tissue 130. For a carbon ion beam, this corresponds to an energy range of about 100-450 MeV/u. The energy of the beam can be changed to control the target depth of a dosage. For example, a 135 MeV/u beam penetrates about 4 cm of water; a 270 MeV/u beam penetrates about 15 cm of water; and a 330 MeV/u beam penetrates about 20 cm of water.

Figure 2:
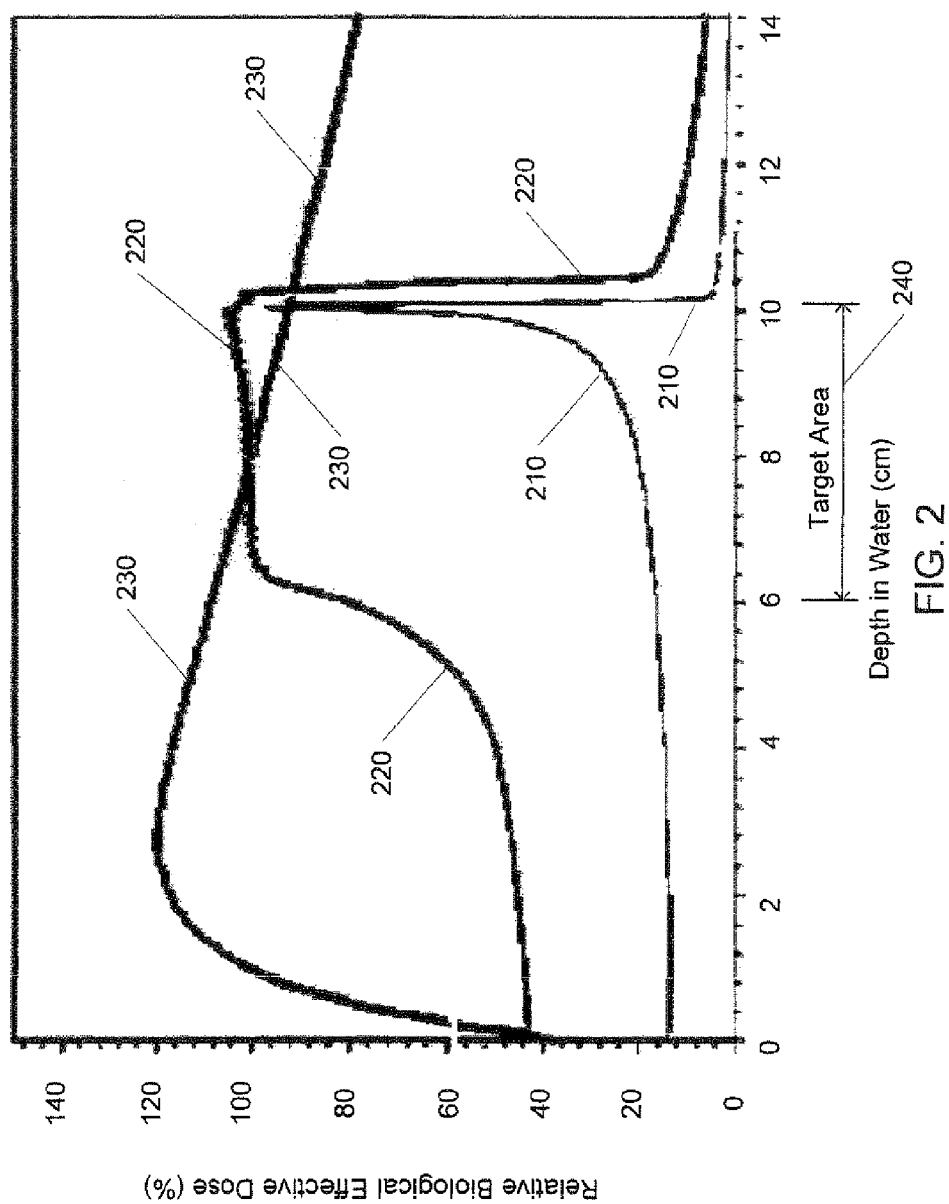
FIG. 2 is a graph of the relative biological effective dose of various particles in accordance with an illustrative embodiment.

Referring now to FIG. 2, a graph of the relative biological effective dose of various particles in accordance with an illustrative embodiment is shown. Plot 210 is a graph of the relative biological effective dose (%) of mono-energetic carbon ions versus the depth of the ion in water (cm). Plot 210 shows that the relative biological effective dose peaks at the Bragg peak which occurs at about 10 cm. Plot 220 is a graph of the relative biological effective dose (%) of carbon ions in a range of energies versus the depth of the ion in water (cm), where the ion energies are modulated to form a spread-out Bragg peak (SOBP). The SOBP occurs from about a depth of 6 cm to about 10 cm. Thus, the energy and spread of the ions can be selected to match a target area 240. For comparison, plot 230 is a graph of the relative biological effective dose (%) of high energy photons versus the depth of the photons in water (cm). The effective dose of the photons is expended closer to the surface (i.e., 0 cm) and does not exhibit a sharp peak. Hence, ions can be used to target areas at greater depths with more precision than photons.

Referring again to FIG. 1, after traveling a distance in the tissue 130, the ions of ion beam 110 eventually come to rest, for example, at point 140. At least some of the ions of ion beam 110 can also be positron emitters as described above. The positron emitters can emit a positron 150. For example, Carbon-11 has a half-life of about 20 min, Nitrogen-13 has a half-life of about 10 min, Oxygen-15 has a half-life of about 2 min, and Fluorine-18 has a half-life of about 110 min. The isotope can be chosen to provide the desired duration of dosage. The majority of electron-positron decays create two 511 keV gamma photons almost exactly antiparallel to each other. The 511 keV gamma photons can be the basis of positron emission tomography (PET) spatial calculations. An electron 155 in the tissue 130 annihilates with the positron 150 to produce a gamma ray 160. The gamma ray 160 can damage a cell 170. For example, the DNA and/or RNA of cell 170 can be damaged, the mitochondria of cell 170 can be damaged, etc. Cell 170 can experience cell death as a result of the damage. In addition, gamma rays from the positron emitters can be used to determine the dosage and treatment area as explained further below.

Advantageously, the radioisotope ion beam gamma therapy localizes gamma ray emissions to the target area by delivering positron emitters directly to the target area. The proton emitters provide treatment both by ionization and gamma emission thereby producing a synergistic effect. Advantageously, the ionization provides an immediate therapeutic effect and the gamma emission provides a secondary therapeutic effect.

Figure 3:
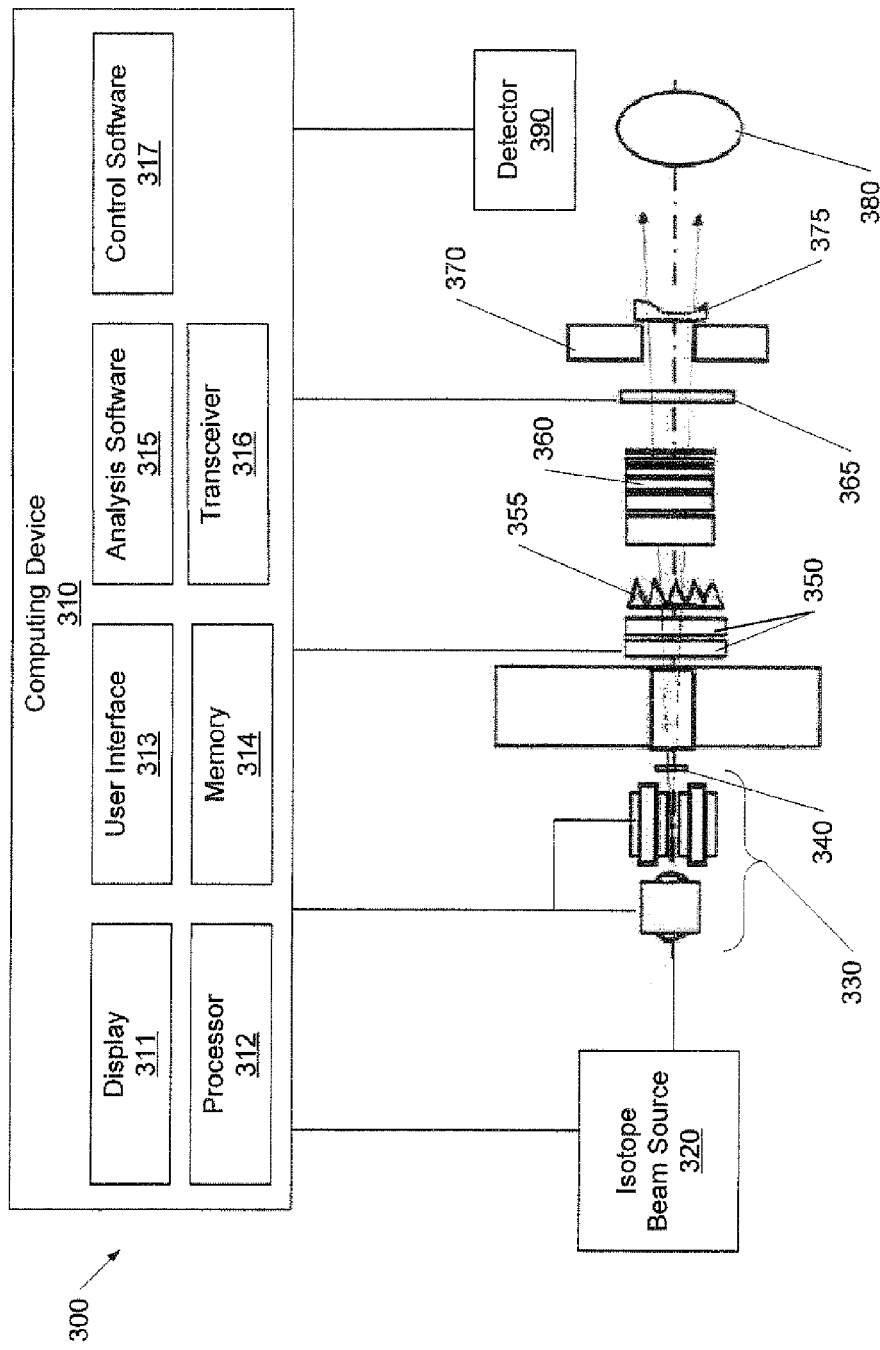
FIG. 3 is a schematic of a radioisotope ion beam gamma therapy system in accordance with an illustrative embodiment.

Referring to FIG. 3, a schematic of a radioisotope ion beam gamma therapy system 300 in accordance with an illustrative embodiment is shown. The radioisotope ion beam gamma therapy system 300 includes a computing device 310, an isotope beam source 320, a wobbler magnet 330, a scatterer 340, a monitor 350, a ridge filter 355, a range shifter 360, a flatness monitor 365, a collimator 370, a range compensator 375, and a detector 390. The beam line can be shielded with, for example, but not limited to, lead. The radioisotope ion beam gamma therapy system 300 can direct an ionized isotope beam at a target 380.

The isotope beam source 320 can be used to generate ions and short-lived, positron-emitting radioisotopes including, but not limited to, $^{11}$C (Carbon-11), $^{13}$N (Nitrogen-13), $^{15}$O (Oxygen-15), and $^{18}$F (Fluorine-18). The isotope beam source 320 can include a synchrotron, a cyclotron, and a linear accelerator. The isotopes can be created, for example, by neutron bombardment in a reactor or proton bombardment in an accelerator. In one embodiment, the isotopes can be created at a facility specialized in the creation of medical isotopes. The isotopes can be sputtered or evaporated, ionized, and accelerated in a magnetic field forming an ion beam at least partially including short-lived, positron-emitting radioisotopes. The strength of the magnetic field can be changed to control the exit velocity of the ions in the beam.

The beam enters the wobbler magnet 330 that controls the direction of the beam by altering the magnetic field along a vertical and horizontal axis. Thus, the wobbler magnet 330 can spontaneously deflect the beam vertically and horizontally so that the beam can be pointed in a specific area. Alternatively, the wobbler magnet 330 can be controlled by computing device 310 to scan a target area of the target 380.

The directed beam enters the scatterer 340. The scatterer 340 evens out the ion fluence. Monitor 350 detects the ion fluence and provides control feedback to the isotope beam source 320.

Ridge filter 355 evens out the velocity of the ions in the directed beam by removing the low speed and high speed ions. By removing the low speed and high speed ions, the penetration depth and profile of the ions can be controlled. The range shifter 360 dynamically controls the depth of the ion penetration relative to the ridge filter 355. Flatness monitor 365 detects the profile of the filtered and shifted beam. Collimator 370 aligns the ion trajectories and the range compensator 375 corrects for any depth variances within the target area of the target 380.

After leaving the range compensator 375, the conditioned ion beam strikes the target 380. As described above, short-lived, positron-emitting radioisotopes in the beam can ionize atoms as the positron-emitting radioisotopes come to rest within the target area of the target 380. The positron-emitting radioisotopes can then emit a positron which can annihilate with an electron to produce a gamma ray.

Computing device 310 can be a circuit, a desktop computer, a laptop computer, a cloud computing client, a handheld computing device, or other type of computing device known to those of skill in the art. Computing device 310 includes, a memory 314, control software 317, analysis software 315, a processor 312, a display 311, and a user interface 313. In alternative embodiments, computing device 310 may include fewer, additional, and/or different components. Memory 314, which can be any type of permanent or removable computer memory known to those of skill in the art, can be a computer-readable storage medium. Memory 314 is configured to store control software 317, analysis software 315, an application configured to run control software 317 and analysis software 315, captured data, and/or other information and applications as known to those of skill in the art. Transceiver 316 of computing device 310 can be used to receive and/or transmit information through a wired or wireless network as known to those of skill in the art. Transceiver 316, which can include a receiver and/or a transmitter, can be a modem or other communication component known to those of skill in the art.

Analysis software 315 is configured to analyze captured gamma ray data from detector 390 and determine the location of the target area and/or the dosimetry of the radioisotope ion beam gamma therapy. The captured data can be received by computing device 310 through a wired connection such as a USB cable and/or through a wireless connection, depending on the embodiment. The captured data may include the gamma ray data before, during, and after application of the ion beam including positron emitters. Analysis software 315, which can be implemented as computer-readable instructions configured to be stored on memory 314, can analyze the captured data to locate a target area as in a PET scan and can determine a concentration of positron emitters, as described further below.

In one illustrative embodiment, analysis software 315 can include a computer program and/or an application configured to execute the program such as Matlab. Alternatively, other programming languages and/or applications known to those of skill in the art can be used. In one embodiment, analysis software 315 can be a dedicated standalone application. Processor 312, which can be in electrical communication with each of the components of computing device 310, can be used to run the application and to execute the instructions of analysis software 315. Any type of computer processor(s) known to those of skill in the art may be used.

In one illustrative embodiment, analysis software 315 can determine the location of a target area by detecting gamma radiation from an administered radioactive tracer. For example, a patient is given a radioactive tracer. More radioactive material accumulates in areas that have higher levels of chemical activity. Detector 390 images gamma emissions from the radioactive tracer. This often corresponds to areas of disease and shows up as brighter spots on a PET scan. For example, cancer cells show up as brighter spots on PET scans because they have a higher metabolism rate than do normal cells. Hence, the gamma emissions from the radioactive tracer can be used to determine the boundaries of the target area for treatment. Optionally, a PET scan can be done passively depending on the ion dosage. Optionally, active PET scans can be adapted to account for any radiation already present from the therapeutic. Alternatively, other imaging techniques can be used to determine the boundaries of the target area for treatment. For example, other targeting methods can include, but are not limited to, radiation tomography, gamma ray photography, or any kind of radiation scan.

In another illustrative embodiment, analysis software 315 can determine the dosimetry of the radioisotope ion beam gamma therapy. As discussed above, after the positron emitters from the ion beam come to rest, the positron-emitting radioisotopes can then emit positrons which can annihilate with electrons to produce gamma rays. Detector 390 images gamma emissions from the positron annihilation. Thus, the concentration of the positron-emitting radioisotopes can be determined based on the amount of gamma radiation detected. In addition, the dosage profile of the target area can be determined. Hence, the analysis software 315 can determine if the proper dosage has been applied throughout the target area. In addition, the analysis software 315 can account for tissue type, beam path, beam type, and beam fluence.

Dosimetry of combined beam ionization and gamma ray emission can follow existing methods, for example, such as those outlined by the International Atomic Energy Agency for clinical dosimetry. International Atomic Energy Agency (Ed.), "Absorbed Dose Determination in External Beam Radiotherapy," Technical Report Series No. 398 (IRS-398). Dosimetry can also be determined empirically with respect to the energy absorbed by a specific material. Nonradioactive carbon beams have established protocols as described in Hartmann, G. H., et al., "Determination of Water Absorbed Dose in a Carbon Ion Beam Using Thimble Ionization Chambers," Physics in Medicine and Biology (1999) 44: 1193-1206.

Control software 317 is configured to control, for example, the isotope beam source 320, the wobbler magnet 330, and range shifter 360. The isotope beam source 320, the wobbler magnet 330, and range shifter 360 can be communicatively coupled to computing device 310 through a wired connection such as a USB cable and/or through a wireless connection, depending on the embodiment. Control software 317, which can be implemented as computer-readable instructions configured to be stored on memory 314, can control the positioning and implantation profile of the ion beam including positron emitters.

In one illustrative embodiment, control software 317 can include a computer program and/or an application configured to execute the program such as Windows available from Microsoft Corp., Redmond, Wash. Alternatively, other programming languages and/or applications known to those of skill in the art can be used. In one embodiment, control software 317 can be a dedicated standalone application. Processor 312, which can be in electrical communication with each of the components of computing device 310, can be used to run the application and to execute the instructions of control software 317. Any type of computer processor(s) known to those of skill in the art may be used.

In one illustrative embodiment, control software 317 can control the average velocity of the ions in the ion beam by controlling the magnetic field of the isotope beam source 320. The control software 317 can control the direction of the ions in the ion beam by controlling the magnetic field of the wobbler magnet 330. The control software 317 can control the depth (i.e., Bragg peak) of the dosage profile of the ion beam by moving the range shifter 360 relative to the target area. The isotope beam source 320, the wobbler magnet 330, and range shifter 360 can be controlled to scan the ion beam including positron emitters through the target area. Alternatively, with regard to other isotope beam sources, beam control is performed according to the control mechanisms available.

In another illustrative embodiment, control software 317 uses feedback from analysis software 315 to control the ion beam including positron emitters. For example, if the analysis software 315 determines that a particular area of the target area has not received enough dosage, the control software 317 can hold or re-sweep the beam at the particular point.

Display 311 of computing device 310 can be used to display one or more images of data from detector 390, a user interface window through which a user can control analysis software 315 and control software 317, etc., plots illustrating the dosage and dosage regiment, etc. Display 311 can be a liquid crystal display, a cathode ray tube display, or other type of display known to those of skill in the art. User interface 313 allows a user to interact with computing device 310 and to enter information into the user interface window. User interface 313 can include a mouse, a keyboard, a touch screen, a touch pad, etc. The user can use user interface 313 to control the on/off status of the detector 390 and the beam.

In the embodiment illustrated with reference to FIG. 3, the computing device 310, the isotope beam source 320, the wobbler magnet 330, the scatterer 340, the monitor 350, the ridge filter 355, the range shifter 360, the flatness monitor 365, the collimator 370, the range compensator 375, and the detector 390 are illustrated as separate components that are combined to form the radioisotope ion beam gamma therapy system 300. In an alternative embodiment, any or all of the components of radioisotope ion beam gamma therapy system 300 may be integrated into a dedicated stand-alone apparatus that has the functionality described with reference to FIG. 3.

Examples of systems that can be adapted for radioisotope ion beam gamma therapy are particle accelerators for generating carbon ions (non-radioactive), coupled to a beam irradiation system including a wobbler magnet (for focusing), filters (to change spatial and energy characteristics), and/or a collimator. An example particle accelerator for generating carbon ions is the heavy-ion medical accelerator complex (HIMAC) at the National Institute of Radiological Sciences in Chiba, Japan. The adapted beam system would also include shielding and handling equipment to account for the radioactive isotopes generated. The shielding could be relatively weak since the isotopes to be generated would have short half-lives.

Figure 4:
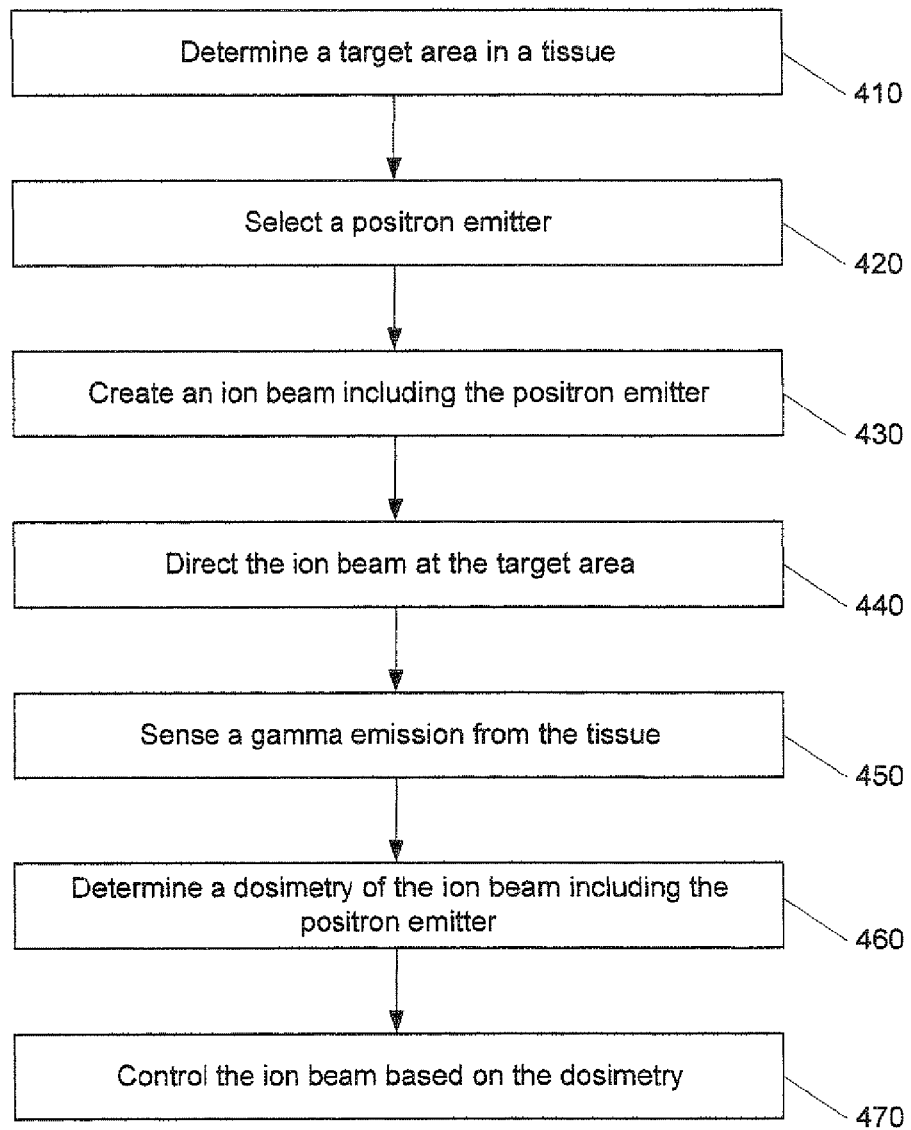
FIG. 4 is a flow diagram illustrating operations performed to provide radioisotope ion beam gamma therapy in accordance with an illustrative embodiment.

Referring to FIG. 4, a flow diagram illustrating operations performed to provide radioisotope ion beam gamma therapy in accordance with an illustrative embodiment is shown. In alternative embodiments, fewer, additional, and/or different operations may be performed. In an operation 410, a target area in a tissue can be determined. The target area can include, for example, a cancerous area such as, but no limited to, a tumor. The target area can be located, for example, using a PET scan.

In an operation 420, a positron emitter can be selected. The positron emitter can be a short-lived, positron-emitting radioisotope including, but not limited to, $^{11}$C (Carbon-11), $^{13}$N (Nitrogen-13), $^{15}$O (Oxygen-15), and $^{18}$F (Fluorine-18). The positron emitter can be an isotope of an element with an atomic number less than neon; however, other isotopes can be used. The positron emitter can be selected based on the particular tissue to be irradiated. For example, Fluorine-18 can be selected where the type of cancer to be treated needs a relatively long-term exposure to radiation in order to be effective. Without wishing to be bound to a particular theory, it may be postulated that a long living positron-emitting radioisotope, such as Fluorine-18, can be best suited for cancers that are treated using brachytherapy, such as, but not limited to, cervical cancer, prostate cancer, breast cancer, and skin cancer.

One or more isotopes can be selected. For example, a first positron emitter (e.g., Carbon-11) and a second positron emitter (e.g., Fluorine-18) can be selected. The first positron emitter can be selected to treat a first type of carcinoma and the second positron emitter can be selected to treat a second type of carcinoma. Different tissues and cancers react differently to the different isotopes. Without wishing to be bound to a particular theory, it may be postulated that diffuse tissues, such as lung cancer tissue, can respond better to slow-moving, larger isotopes that have more time to interact with a tissue. Additionally, dense, solid cancer tissues can respond better to larger isotopes, such as isotopes with an atomic number of six or higher, since the dense cancer tissues can absorb a significant amount of energy. Furthermore, electronegative elements may interact less with a hypoxic tissue compared to elements such as carbon. Other chemical attributes of the particular elements used as positron emitters and the tissues treated may also effect the interaction of the particular elements and the tissues treated.

In addition, different positron emitters can be selected where various penetration depths are desired. Typically, particle accelerators are configured to accommodate a relatively narrow depth range in order to maintain good process control. By using a second positron emitter, the range of depths possible in a single firing are increased while still maintaining good process control.

In an operation 430, an ion beam including the selected positron emitter can be created. For example, a synchrotron, a cyclotron, or a linear accelerator can be used to form an ion beam by accelerating the positron emitters and other ions through a magnetic field. In an operation 440, the ion beam can be directed at the target area as described above with reference to FIG. 3. When the ions of the ion beam strike the target area, short-lived, positron-emitting radioisotopes in the beam can ionize atoms as the positron-emitting radioisotopes come to rest within the target area of the target. The ionization radiation can cause cell damage which can lead to cell death. The positron-emitting radioisotopes can then emit a positron which can annihilate with an electron to produce a gamma ray. The gamma rays can cause cell damage which can lead to cell death.

In an operation 450, gamma emissions from the tissue are sensed, for example, by a detector. Data generated from the gamma emissions can be used to image the area exposed to the positron emitters. In an operation 460, a dosimetry of the ion beam including the positron emitter can be determined using data from the gamma emissions and/or information from the creation of the ion beam, for instance, the beam energy. Generally, a greater concentration of gamma emissions indicates a higher dosage. During a treatment, dosage data is collected for control and later analysis.

In an operation 460, the ion beam is controlled based on the dosimetry. For example, if the target area has not received enough dosage, the ion beam can hold or re-sweep the beam at the particular point. Thus, the controlled ion beam can restrict positron emitter implantation to the target area.

Advantageously, the radioisotope ion beam gamma therapy localizes gamma ray emissions to the target area by delivering proton emitters directly to the target area. The proton emitters provide treatment both by ionization and gamma emission thereby producing a synergistic effect. Advantageously, the ionization provides an immediate therapeutic effect and the gamma emission provides a secondary therapeutic effect.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to, physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method comprising:
   directing an ion beam at a tissue;
      wherein the ion beam comprises positron-emitting ions prior to contact with the tissue, at a dosage sufficient to ionize at least a portion of the tissue and to damage at least one cell in at least the portion of the tissue;
   imaging at least the portion of the tissue using a positron emission tomography system, wherein the positron emission tomography system detects gamma rays associated with the positron-emitting ions;
   selecting a target position on the tissue for the ion beam based on the detected gamma rays;
   determining a dosage for the ion beam based on the detected gamma rays; and controlling an average velocity of ions in the ion beam based on the determined dosage and a magnetic field of the ion beam.

2. The method of claim 1, wherein the positron-emitting ions comprise at least one isotope of an element of the positron-emitting ions including at least one of: carbon-11, nitrogen-13, oxygen-15, and fluorine-18.

3. The method of claim 2, wherein the isotope has an atomic number less than 11.

4. The method of claim 1, further comprising:
generating the ion beam with at least one of: a cyclotron, a synchrotron, or a particle accelerator; and
wherein directing an ion beam at the tissue comprises targeting at least the portion of the tissue using at least one of: a stereotactic targeting system, clinical dosimetry system, or the positron emission tomography system, wherein the ion beam is controlled such that a delivered energy of the ions peaks throughout a volume of the portion of the tissue.

5. The method of claim 1, wherein the dosage is sufficient to cause positrons produced, in vivo, by the positron-emitting ions to combine with electrons to create gamma rays that damage the at least one cell in the course of a combination ion beam therapy and brachytherapy treatment.

6. The method of claim 5, wherein the damage associated with the positron-emitting ions comprises damage to deoxyribonucleic acid (DNA) of the at least one cell, and the damage associated with the gamma rays comprises damage to the DNA of the at least one cell; and
wherein the positron-emitting ions prevent replication of the at least one cell, and wherein at least the portion of the tissue is cancerous.

7. The method of claim 1, further comprising removing low speed ions and high speed ions in the ion beam to control the average velocity of the ion beam.

8. An apparatus comprising:
an ion beam apparatus configured to generate and to direct an ion beam at a tissue;
wherein the ion beam includes positron-emitting ions prior to contact with the tissue, at a dosage sufficient to ionize at least a portion of the tissue and to damage at least one cell in at least the portion of the tissue;
a positron emission tomography system configured to image at least the portion of the tissue, wherein the positron emission tomography system detects gamma rays associated with the positron-emitting ions; and
a targeting system configured to:
select a target position on the tissue for the ion beam based on the detected gamma rays;
determine a dosage for the ion beam based on the detected gamma rays; and
control an average velocity of ions in the ion beam based on the determined dosage and a magnetic field of the ion beam.

9. The apparatus of claim 8, wherein the targeting system comprises at least one of: a stereotactic targeting system, clinical dosimetry system, or the positron emission tomography system, wherein the targeting system is configured to control the ion beam such that a delivered energy of the positron-emitting ions peaks throughout a volume of the portion of the tissue.

10. The apparatus of claim 8, wherein the positron-emitting ions comprise at least one isotope of an element of the positron-emitting ions including at least one of: carbon-11, nitrogen-13, oxygen-15, and fluorine-18.

11. The apparatus of claim 10, wherein the isotope has an atomic number less than 11.

12. The apparatus of claim 8, wherein the ion beam apparatus comprises at least one of: a cyclotron, a synchrotron, a particle accelerator, a focusing device, filters, collimators, and radiation shielding.

13. The apparatus of claim 8, wherein the dosage is sufficient to cause positrons produced, in vivo, by the positron-emitting ions to combine with electrons to create gamma rays that damage the at least one cell in the course of a combination ion beam therapy and brachytherapy treatment.

14. The apparatus of claim 13, wherein the damage associated with the positron-emitting ions comprises damage to deoxyribonucleic acid (DNA) of the at least one cell, and the damage associated with the gamma rays comprises damage to the DNA of the at least one cell; and
wherein the positron-emitting ions prevent replication of the at least one cell, and wherein at least the portion of the tissue is cancerous.

15. The apparatus of claim 13, wherein the positron emission tomography system is configured to:
detect the gamma rays associated with the positron emitters;
image at least the portion of the tissue based on the detected gamma rays; and
control a direction and an energy of the ion beam based on the gamma-ray dosage and the image.

16. A non-transitory computer-readable medium having computer readable instructions stored thereon that, when executed by a computing device, cause the computing device to perform operations comprising:
directing an ion beam at a tissue;
wherein the ion beam comprises positron-emitting ions prior to contact with the tissue, at a dosage sufficient to ionize at least a portion of the tissue and to damage at least one cell in at least the portion of the tissue;
imaging at least the portion of the tissue to detect gamma rays associated with the positron-emitting ions;
selecting a target position on the tissue for the ion beam based on the detected gamma rays;
determining a dosage for the ion beam based on the detected gamma rays; and
controlling an average velocity of ions in the ion beam based on the determined dosage and a magnetic field of the ion beam.

17. The non-transitory computer-readable medium of claim 16, wherein the positron- emitting ions comprise at least one isotope of an element of the positron-emitting ions including at least one of: carbon-11, nitrogen-13, oxygen-15, and fluorine-18.

18. The non-transitory computer-readable medium of claim 16, wherein the computer readable instructions, if executed by the computing device, further cause the computing device to perform operations comprising:
collecting gamma ray data associated with the positron-emitting ions;
imaging at least the portion of the tissue based on the gamma ray data; and
controlling a direction and an energy of the ion beam based on the gamma-ray dosage and the image.

19. The non-transitory computer-readable medium of claim 16, wherein the dosage is sufficient to cause positrons produced, in vivo, by the positron-emitting ions to combine with electrons to create gamma rays that damage the at least one cell in the course of a combination ion beam therapy and brachytherapy treatment.

20. The non-transitory computer-readable medium of claim 19, further comprising determining a target area of the tissue;

wherein directing the ion beam at the tissue comprises directing the ion beam at the target area;

wherein the damage associated with the positron-emitting ions comprises damage to deoxyribonucleic acid (DNA) of the at least one cell, and the damage associated with the gamma rays comprises damage to the DNA of the at least one cell; and wherein the positron-emitting ions prevent replication of the at least one cell, and wherein the portion of the tissue is cancerous.

* * * * *

UNITED STATES PATENT AND TRADEMARK OFFICE
CERTIFICATE OF CORRECTION

| | | |
|---|---|---|
| PATENT NO. | : 9,220,921 B2 | Page 1 of 1 |
| APPLICATION NO. | : 13/063428 | |
| DATED | : December 29, 2015 | |
| INVENTOR(S) | : Chen | |

It is certified that error appears in the above-identified patent and that said Letters Patent is hereby corrected as shown below:

In the specification

In Column 1, below Title, insert -- CROSS-REFERENCE TO RELATED APPLICATION --.

In Column 1, Lines 5-7, delete "This is a National Stage application of PCT/SG2010/000318, filed Sep. 1, 2010, the entirety of which is hereby incorporated by reference in its entirety." and insert -- This application is a U.S. National Stage filing under 35 U.S.C. § 371 of International Application No. PCT/SG2010/000318, filed on Sep. 1, 2010, which is hereby incorporated by reference in its entirety. --.

In Column 1, Lines 66-67, delete "stored is thereon" and insert -- stored thereon --, therefor.

In Column 6, Line 55, delete "(IRS-398)." and insert -- (TRS-398). --, therefor.

In Column 8, Line 14, delete "but no limited" and insert -- but not limited --, therefor.

In Column 9, Line 17, delete "operation 460," and insert -- operation 470, --, therefor.

Signed and Sealed this
Twelfth Day of April, 2016

Michelle K. Lee
*Director of the United States Patent and Trademark Office*